(12) United States Patent
Takahashi et al.

(10) Patent No.: US 6,261,227 B1
(45) Date of Patent: Jul. 17, 2001

(54) AIR FEEDING DEVICE FOR ENDOSCOPE

(75) Inventors: Noriaki Takahashi; Satoshi Takami, both of Saitama-ken (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/437,140

(22) Filed: Nov. 10, 1999

(30) Foreign Application Priority Data

Nov. 12, 1998 (JP) .................................................. 10-321970
Nov. 16, 1998 (JP) .................................................. 10-325553

(51) Int. Cl.[7] ....................................................... A61B 1/12
(52) U.S. Cl. ........................................... 600/158; 600/560
(58) Field of Search ..................................... 600/158, 159, 600/561

(56) References Cited

U.S. PATENT DOCUMENTS

| 5,006,109 | * | 4/1991 | Douglas et al. | 600/560 |
| 5,063,946 | * | 11/1991 | Wada | 600/560 |
| 5,249,579 | * | 10/1993 | Hobbs et al. | 600/560 |
| 5,360,396 | * | 11/1994 | Chan | 600/560 |
| 5,377,688 | | 1/1995 | Aviv et al. | 600/560 |
| 5,431,150 | * | 7/1995 | Yabe et al. | 600/157 |
| 5,515,860 | | 5/1996 | Aviv et al. | 600/560 |
| 5,643,302 | * | 7/1997 | Beiser et al. | 604/66 |
| 5,676,155 | * | 10/1997 | Novak et al. | 600/560 |

\* cited by examiner

*Primary Examiner*—Robert L. Nasser
*Assistant Examiner*—Charles Marmor, II
(74) *Attorney, Agent, or Firm*—Greenblum & Bernstein, P.L.C.

(57) ABSTRACT

An air feeding device for an endoscope system in which air is compressed in a sealed space and discharged from an outlet of a tube connected to the sealed space which is provided with a pressure sensor that detects a pressure of the air in the sealed space, and a pressure adjusting system that adjusts the pressure of air in the sealed space and a pressure setting device through which an operator is capable of setting a discharge pressure. A memory storing a relationship between a discharge pressure and a pressure in the sealed space is further provided. A pressure controller is also provided, which controls the pressure adjusting system in accordance with the air pressure detected by the pressure sensor and the pressure value set by the pressure setting device.

22 Claims, 15 Drawing Sheets

AIR FEEDING DEVICE FOR ENDOSCOPE

SPECIFICATION

BACKGROUND OF THE INVENTION

The present invention relates to an air feeding device for an endoscope to feed air into body cavity.

Conventionally, an air feeding device for an endoscope has been known. The air feeding device has an air compressor which compresses the air within a sealed space, and by opening/closing a valve connected to the sealed space, the air is fed to the human body cavity through a tube such as a forceps channel of an endoscope. In such an air feeding device, in order to measure the pressure of the air, a Y-shaped tube is provided to branch off a path of the air, and a pressure gauge is connected to the branched path. It is known that, if the length of the tube extending inside the human body cavity and the length of the tube extending toward the pressure gauge are made substantially the same, the pressure of the air discharged from the channel of the endoscope toward the body cavity can be detected accurately by the pressure gauge connected to the Y-shaped tube.

When the pressure of the discharged air (hereinafter, referred to as a discharge pressure) is to be changed, the pressure in the sealed space should be adjusted so that the desired discharge pressure is obtained. In the conventional air feeding device, in order to measure the discharge pressure, the air should actually be discharged. Therefore, the pressure within the sealed space should be adjusted by comparing the, actual discharge pressure with a desired discharge pressure (i.e., a target discharge pressure to be achieved). Due to such a configuration, it is impossible to set the pressure within the sealed space to a value corresponding to the desired discharge pressure in advance, and a large amount of air is discharged uselessly until the actual discharge pressure is adjusted to be a desired value. Further, since the Y-shaped tube is used and the amount of discharged air is increased, once the pressure in the sealed space is reduced, it takes time to raise the pressure in the sealed space.

SUMMARY OF THE INVENTION

It is therefore an object of the invention to provide an improved air feeding device in which the pressure of the sealed space can be set to an appropriate pressure at which the air is discharged at a desired discharge pressure, without discharging the air during the adjustment.

For the above object, according to the present invention, there is provided an air feeding device for an endoscope system in which air is compressed in a sealed space and discharged from an outlet of a tube connected to the sealed space, provided with: a pressure sensor that detects a pressure of the air in the sealed space, a pressure adjusting system that adjusts the pressure of air in the sealed space; a pressure setting device through which an operator is capable of setting a discharge pressure; a memory storing a relationship between a discharge pressure and a pressure in the sealed space; and a pressure controller that controls the pressure adjusting system in accordance with (1) the air pressure detected by the pressure sensor, (2) the discharge pressure set by the pressure setting device and (3) the relationship stored in the memory.

Since the relationship between the pressure of the sealed space and the discharge pressure is stored in the memory, the pressure of the sealed space to be achieved can be determined from the target discharge pressure set through the pressure setting device. Accordingly, it is not necessary to actually discharge the air when the air feeding device is adjusted to discharge the air at the target desired pressure.

Specifically, the relationship includes an approximate expression, and the pressure controller determines the pressure in the sealed space in accordance with the approximate expression and the discharge pressure set through the pressure setting device.

The approximate expression is a polynomial, a linear expression, or a quadratic. If the changeable range of the discharge pressure is limited, a look up table can be used.

Optionally, the pressure adjusting system may include a compressor for feeding external air into the sealed space. In such a case, the pressure adjusting system may be provided with a pressure control valve connected to the sealed space. The pressure control valve is used for discharging the air in the sealed space to reduce the pressure in the sealed space.

Preferably, the pressure adjusting system may be provided with a second pressure sensor for measuring a pressure discharged from the sealed space.

Further, the air feeding device may be provided with an air discharge valve connected between the sealed space and the tube. The air discharge valve is operated to open to discharge the air from the tube such as a forceps channel of an endoscope.

Further optionally, the air feeding device may be provided with a display system which displays the target discharge pressure set through the pressure setting device and the actual discharge pressure detected by the second pressure sensor.

Preferably, the target discharge pressure set through the pressure setting device and the pressure detected by the second pressure sensor are displayed vertically aligned.

Optionally, the discharge pressure set through the pressure setting device is displayed in a first display condition when the discharge pressure is being set but not established or in a second display condition, which is different from the first display condition, when the discharge pressure has been established and is not being set.

Further optionally, a predetermined mark is displayed together with the discharge pressure set through the pressure setting device in the first display condition, while the predetermined mark is extinguished in the second display condition.

Still optionally, the pressure setting device includes a first switch for increasing the discharge pressure and a second switch for decreasing the discharge pressure. The discharge pressure is changed by a predetermined amount upon each operation of the first or second switch, while the discharge pressure is changed subsequently and quickly when the first or second switch is held depressed for longer than a predetermined period.

In a particular case, a mark indicating subsequent change of the discharge pressure is displayed together with the discharge pressure set through the first or second switch when the first or second switch is held depressed for the predetermined period.

Preferably, a latest discharge pressure set by the pressure setting device is displayed as the target discharge pressure set by the pressure setting device until the discharge pressure is set by the pressure setting device.

Further preferably, a latest pressure measured by the second pressure sensor is displayed as the actual discharge pressure measured by the second pressure sensor.

Yet optionally, one of a plurality of units is selectable for displaying the discharge pressure set through the pressure setting device and the pressure measured by the pressure sensor.

The plurality of units may include [mmHg], [Pa] and [Kgf/cm²].

Still optionally, the relationship includes an approximate expression, and the pressure controller determines the pressure in the sealed space in accordance with the approximate expression and the discharge pressure set through the pressure setting device.

The approximate expression can be a polynomial, a linear expression or a quadratic.

DESCRIPTION OF THE ACCOMPANYING DRAWINGS

FIG. 1 schematically shows an entire air feeding system according to a first embodiment of the invention;

FIG. 2 is a rear view of the air feeding device shown in FIG. 1;

FIG. 3 schematically shows an arrangement of main elements inside the air feeding device shown in FIG. 1 when viewed from the top;

Figure 8:
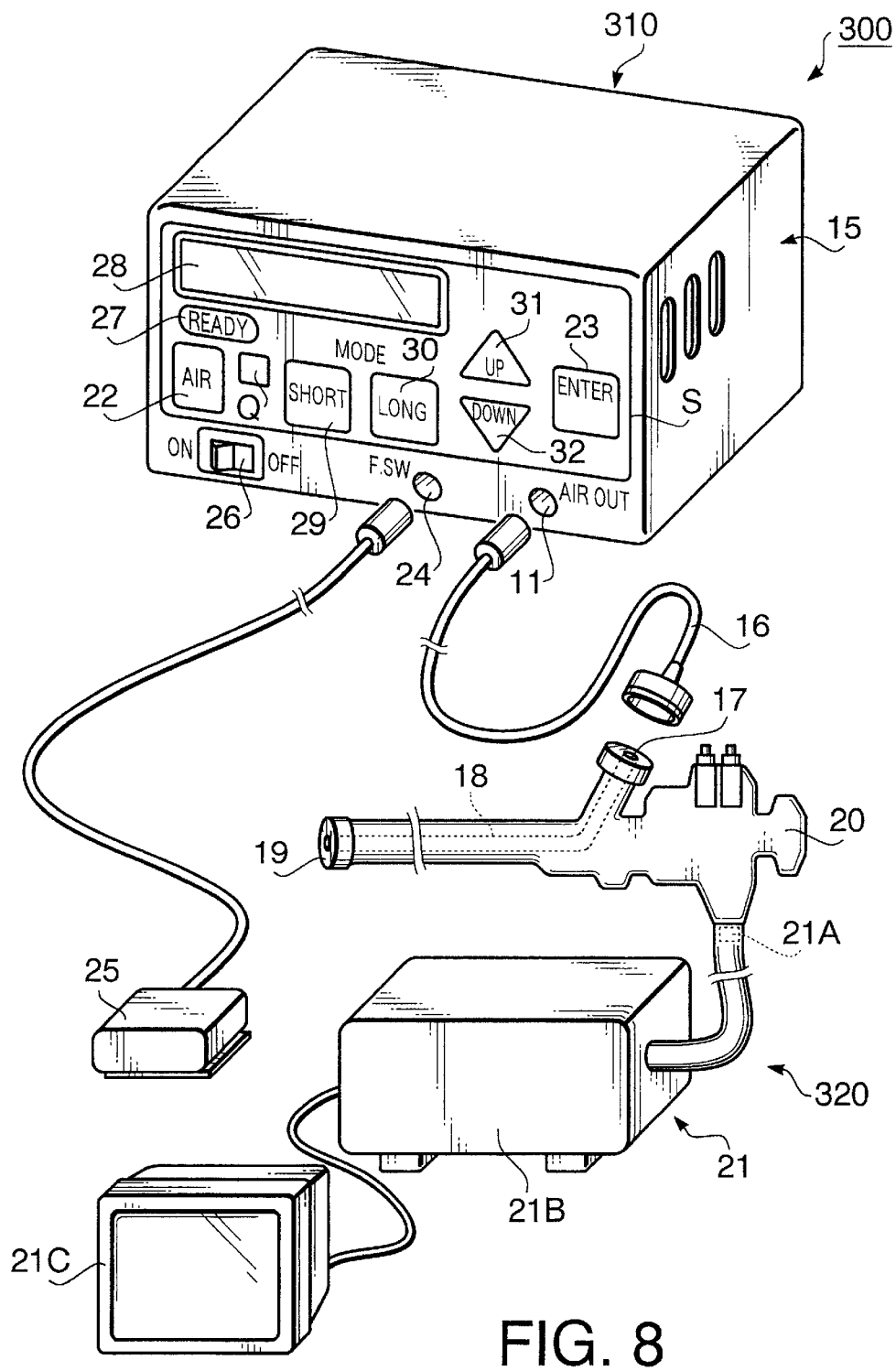
Figure 9A:
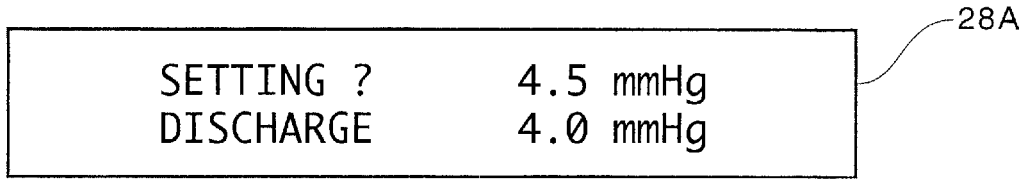
Figure 9B:
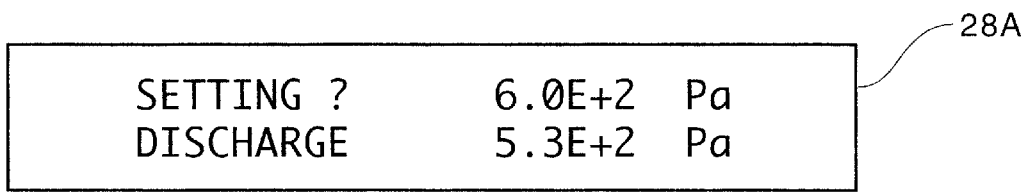
Figure 9C:
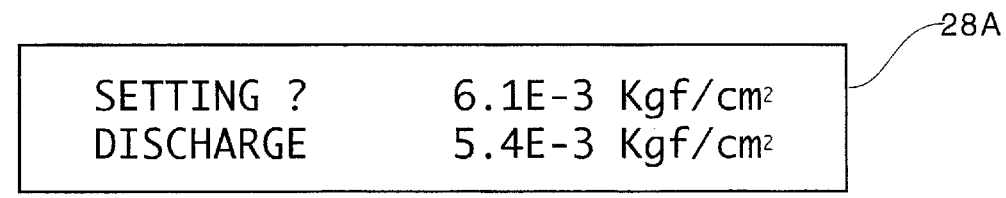
Figure 10:
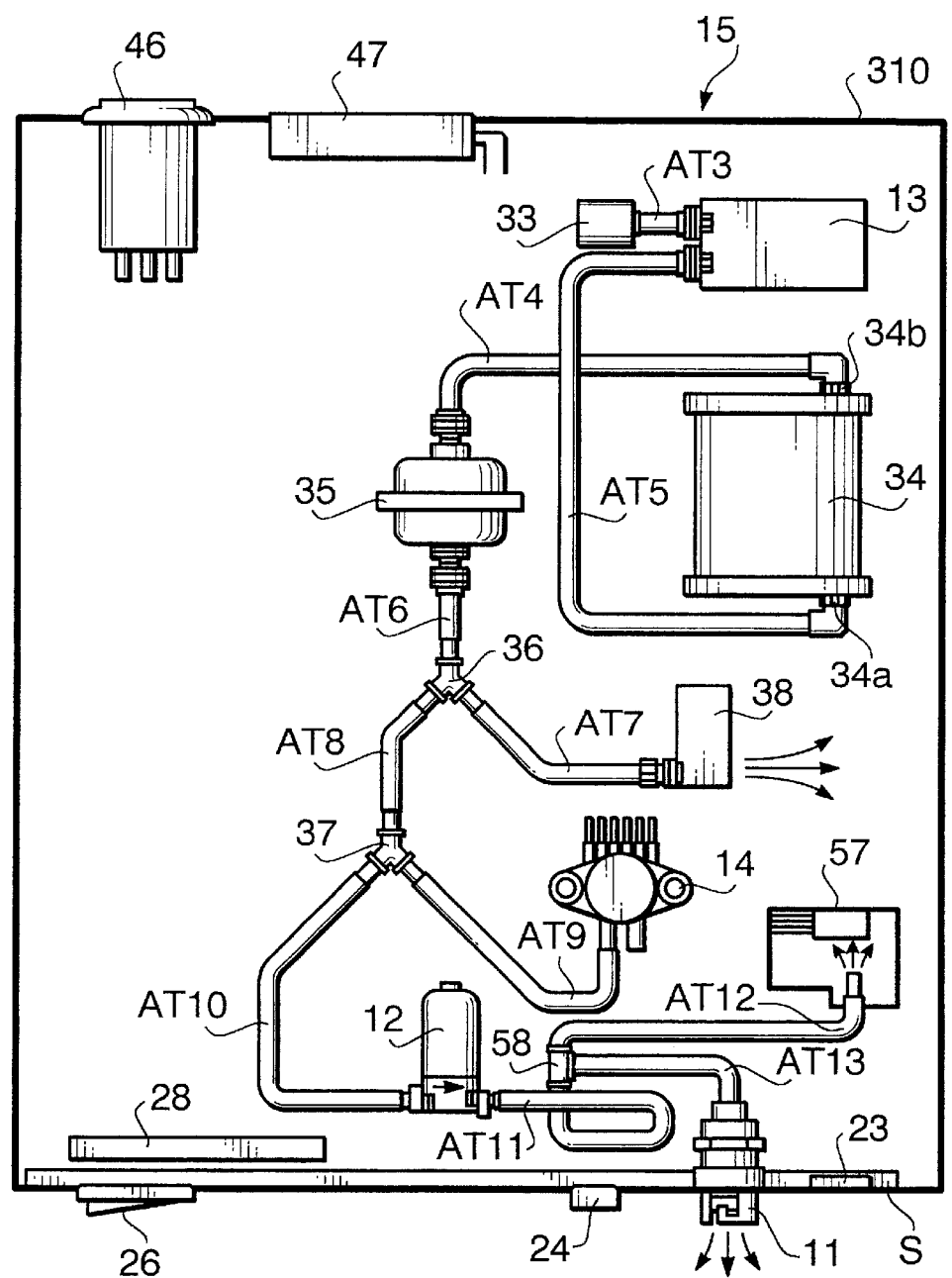
Figure 11:
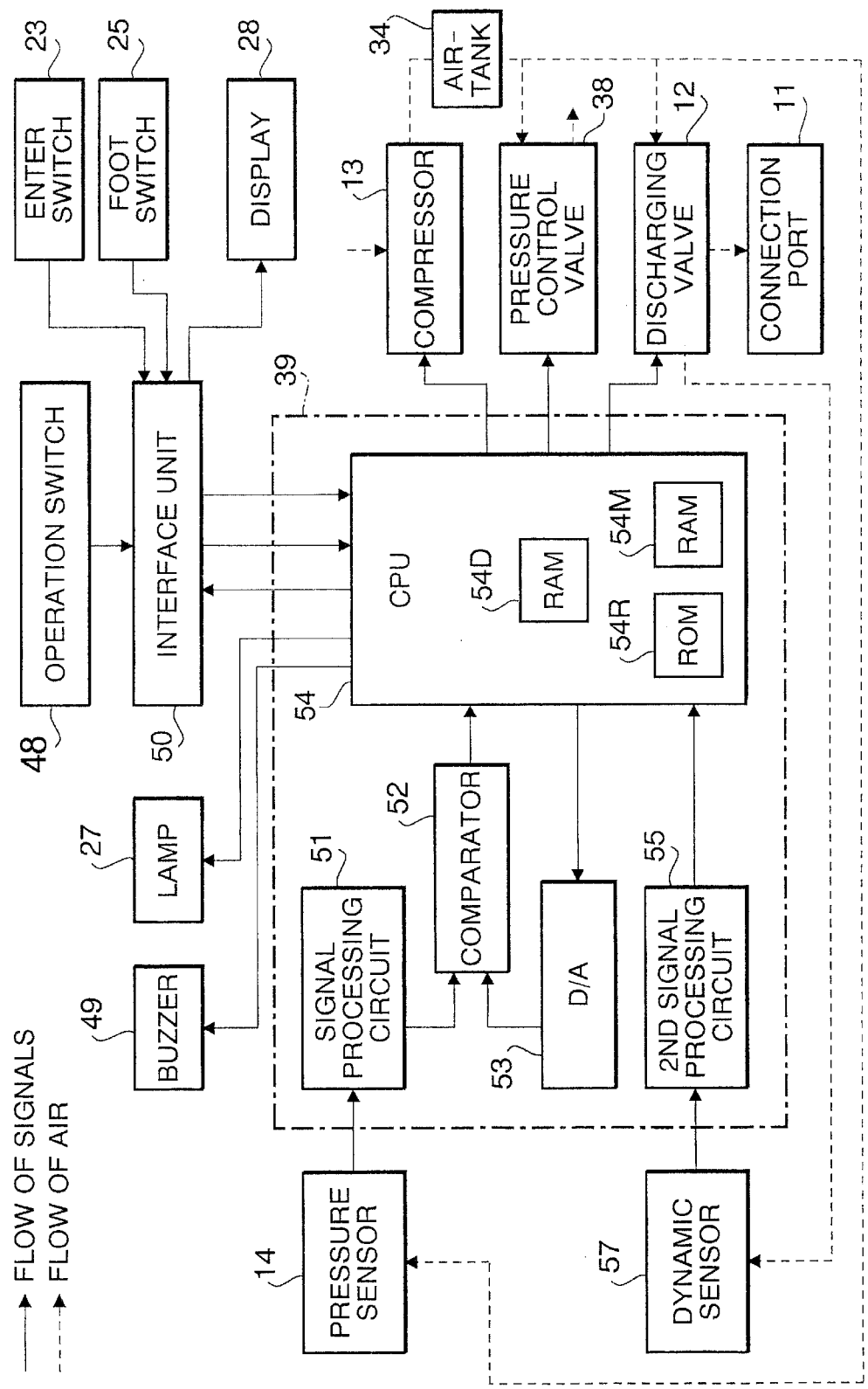
Figure 12:
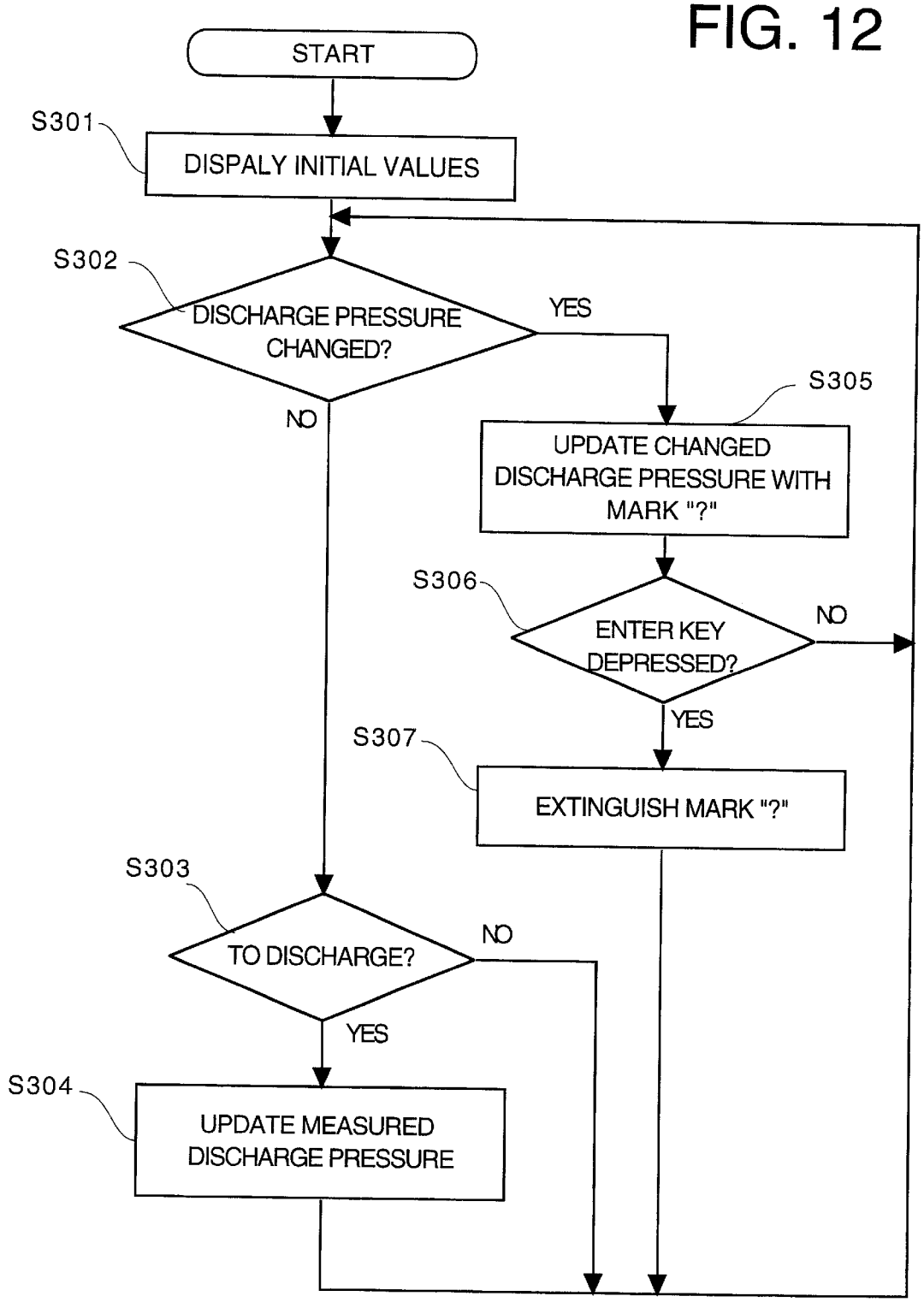
Figure 13:
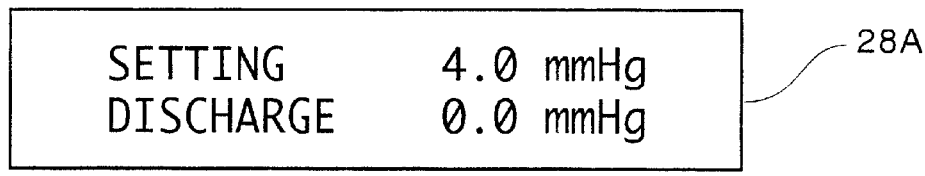
Figure 14A:
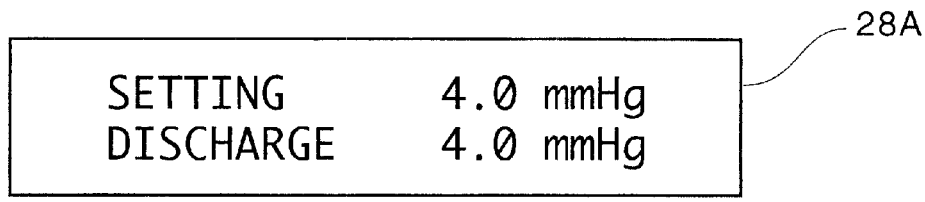
Figure 14B:
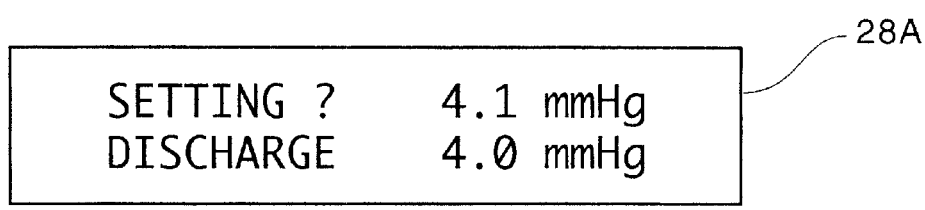
Figure 14C:
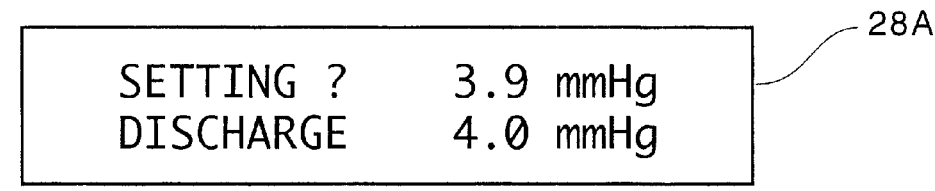
Figure 15A:
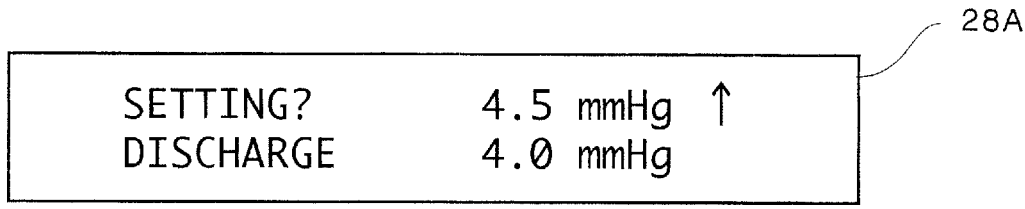
Figure 15B:
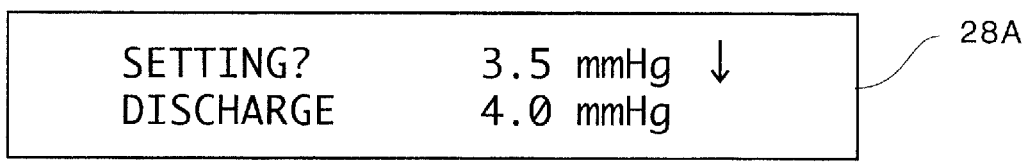
Figure 16A:
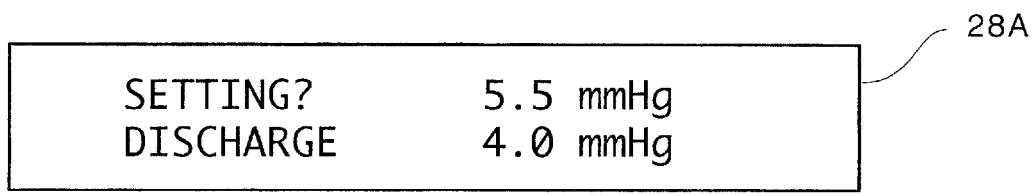
Figure 16B:
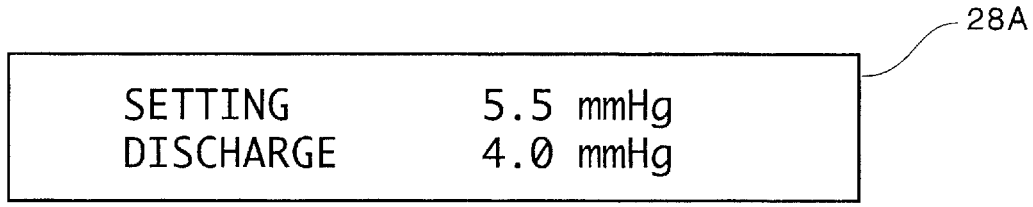
Figure 17A:
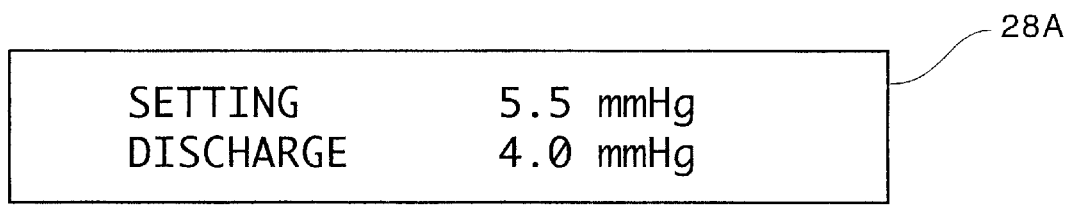
Figure 17B:
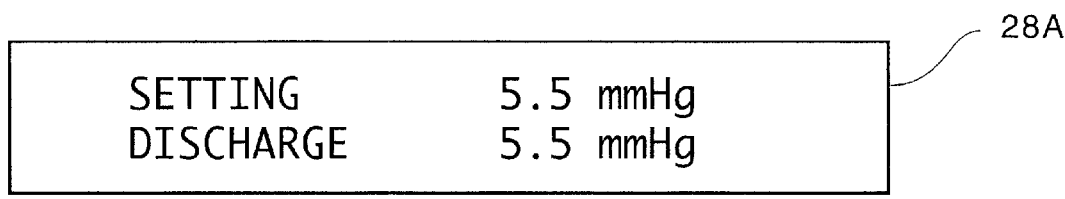

FIG. 8 schematically shows an entire air feeding system according to a third embodiment of the invention;

FIGS. 9A–9C show indication of pressures on a display using different units [mmHg], [Pa] and [Kgf/cm²], respectively;

FIG. 10 schematically shows an arrangement of main elements inside the air feeding device shown in FIG. 8 when viewed from the top;

FIG. 11 is a block diagram illustrating a control system and air flow of the air feeding device according to the third embodiment;

FIG. 12 is a flowchart illustrating the pressure control operation;

FIG. 13 shows indication of pressures on the display;

FIG. 14A shows an exemplary indication of pressures on the display;

FIG. 14B shows indication of pressures on the display when the target discharge pressure is increased;

FIG. 14C shows indication of pressures on the display when the target discharge pressure is decreased;

FIG. 15A shows indication of pressures on the display when the target discharge pressure is increased quickly;

FIG. 15B shows indication of pressures on the display go when the target discharge pressure is decreased quickly;

FIG. 16A shows indication of pressures on the display when the target discharge pressure has been changed and an enter key has not yet been operated;

FIG. 16B shows indication of pressures on the display when the enter key has been operated;

FIG. 17A shows indication of pressures on the display before the air is discharged; and FIG. 17B shows indication of pressures on the display after the air is discharged.

DESCRIPTION OF THE EMBODIMENTS

Hereinafter, the invention will be described with reference to the accompanying drawings.

First Embodiment

Figure 1:
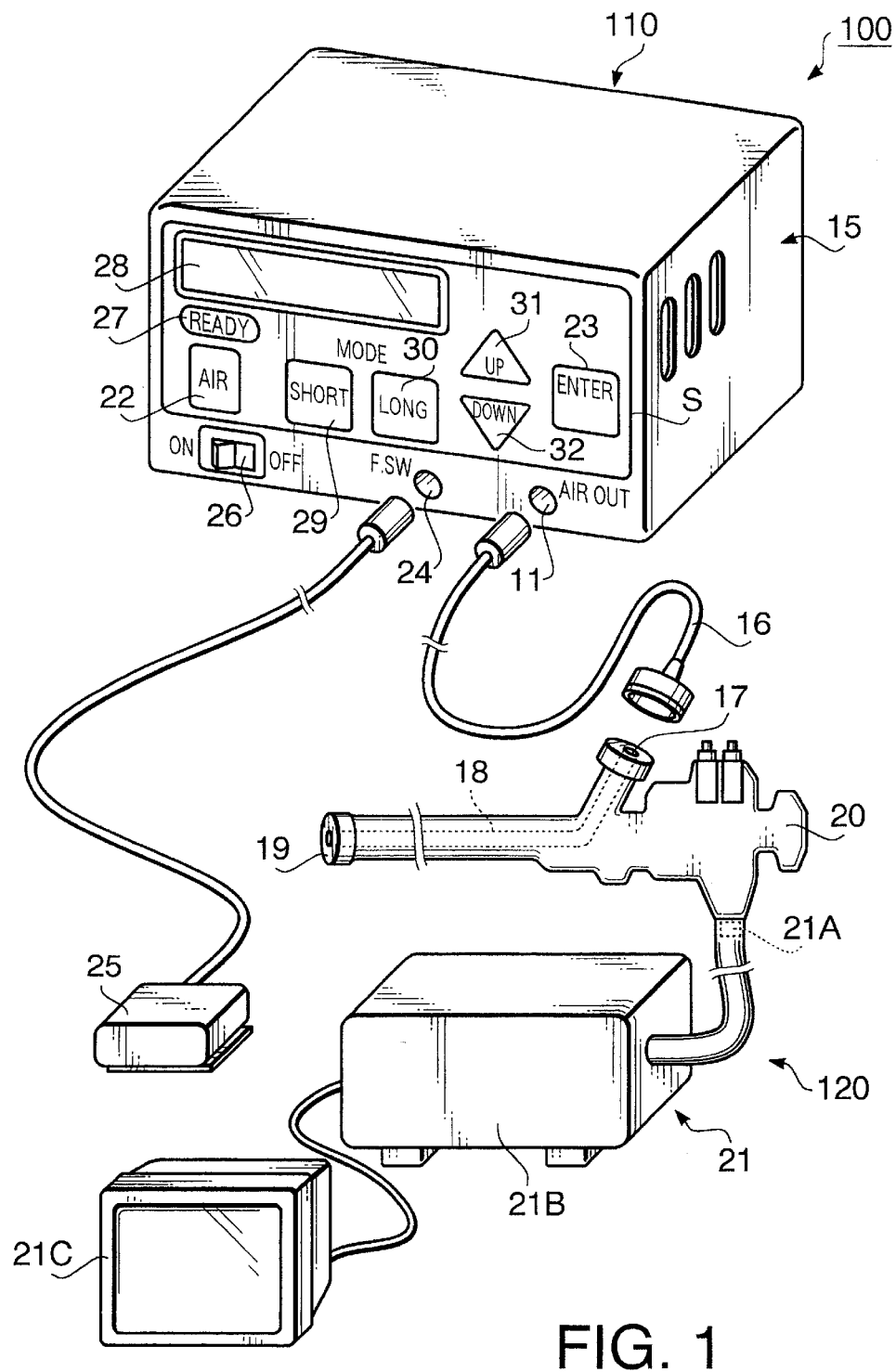

FIG. 1 schematically shows an entire air feeding system 100 according to a first embodiment of the invention.

The air feeding system 100 is provided with an air feeding device 110, and an endoscope system 120. The air is fed by the air feeding system 100 onto the wall of the body cavity for diagnosing thereof.

The air feeding device 110 has a casing 15, on which an operation panel S, a main switch 26, connection ports 11 and 24 are provided.

The main switch 26 is a switch for powering ON/OFF the electrical circuits of the air feeding system 110.

On the operation panel S, an air feeding switch 22 is provided. The air feeding switch 22 is for discharging the air enclosed in a sealed space, which is formed inside the air feeding device 110, to outside thereof. That is, when the air feeding switch 22 is operated, the air is discharged from the connection port 11.

Further, on the operation panel S, a stand-by lamp 27, and a display 28 are provided. The stand-by lamp 27 is lit, when the pressure in the sealed space has reached a pressure at which the air is discharged at a desired pressure, to indicate discharging of the air is ready. The display 28 displays, by alphanumerical characters, information such as the set pressure (a target discharge pressure) of the air. A relationship between the pressure in the sealed space and the discharge pressure will be described later.

Furthermore, on the operation panel S, a short pulse switch 29, a long pulse switch 30, an UP switch 31 and a DOWN switch 32 are provided.

The short pulse switch 29 is used when the air is to be discharged for a relatively shorter period of time. The long pulse switch 31 is a switch for discharging the air for a relatively longer period of time. In this embodiment, when the short pulse switch 29 is depressed, the air is discharged for 60 msec. (milliseconds), while when the long pulse switch 30 is depressed, the air is discharged for one second. The UP and DOWN switches 31 and 32 are used for setting the pressure of the discharged air.

On the operation panel S, further provided is an enter switch 23. The enter switch 23 is used for executing adjustment of the pressure of the sealed space. That is, when the enter switch 23 is ON, the pressure of the sealed space is adjusted to meet the set (target) discharge pressure (i.e., to a pressure at which the target discharge pressure is obtained).

The endoscope system 120 includes an endoscope 20 and an image processor 21. The endoscope 20 is formed with a forceps channel 18. In this system, the air discharged from the air feeding device 110 is introduced in and flows through the forceps channel 18. In order to introduce the air from the air feeding device 110 to the forceps channel 18, a connection tube 16 is used. An end of the connection tube 16 is connected to the connection port 11 of the air feeding device 110, and the other end of the connection tube 16 is connected to the inlet 17 of the forceps channel 18. Thus, the air discharged from the air feeding device 110 flows in the connection tube 16 and the forceps channel 18, and is discharged out of an outlet 19 of the forceps channel 18.

The image processor 21 includes an imaging device 21A for capturing an optical image formed by the endoscope 20 and output an image signal, an signal processing device 21B for processing the image signal, and a display 21C for displaying an image in accordance with the image signal output from the image processing device 21B.

To the connection port 24, a cable of a foot switch 25 for controlling discharge of the air by foot is connected.

Figure 2:
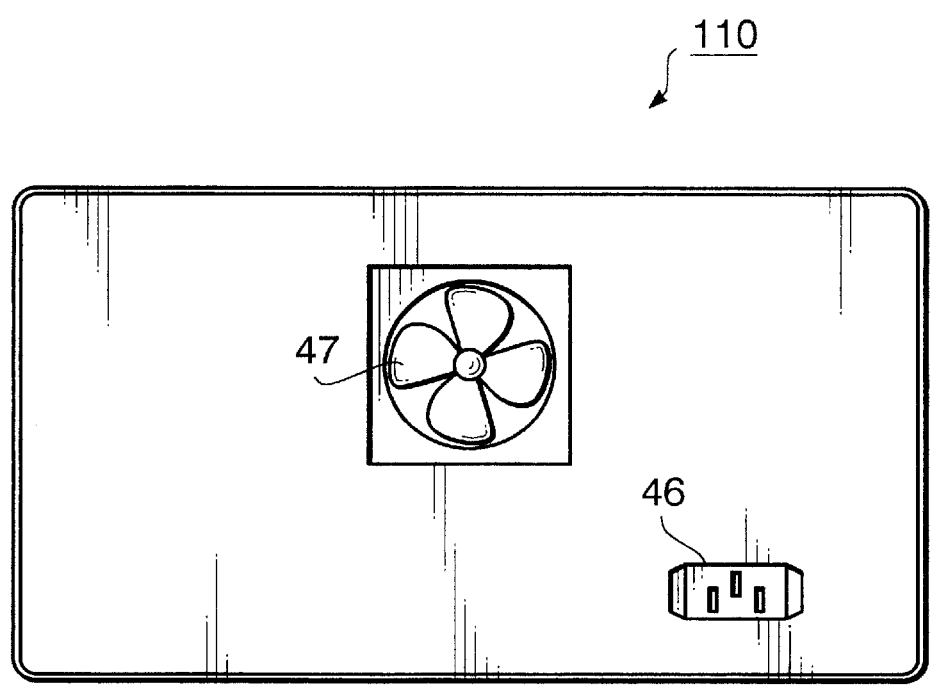

FIG. 2 is a rear view of the air feeding device 110. As shown in FIG. 2, a DC fan 47 for cooling the device 110, and an AC inlet 46 to be connected to a commercial electric power source are provided.

Figure 3:
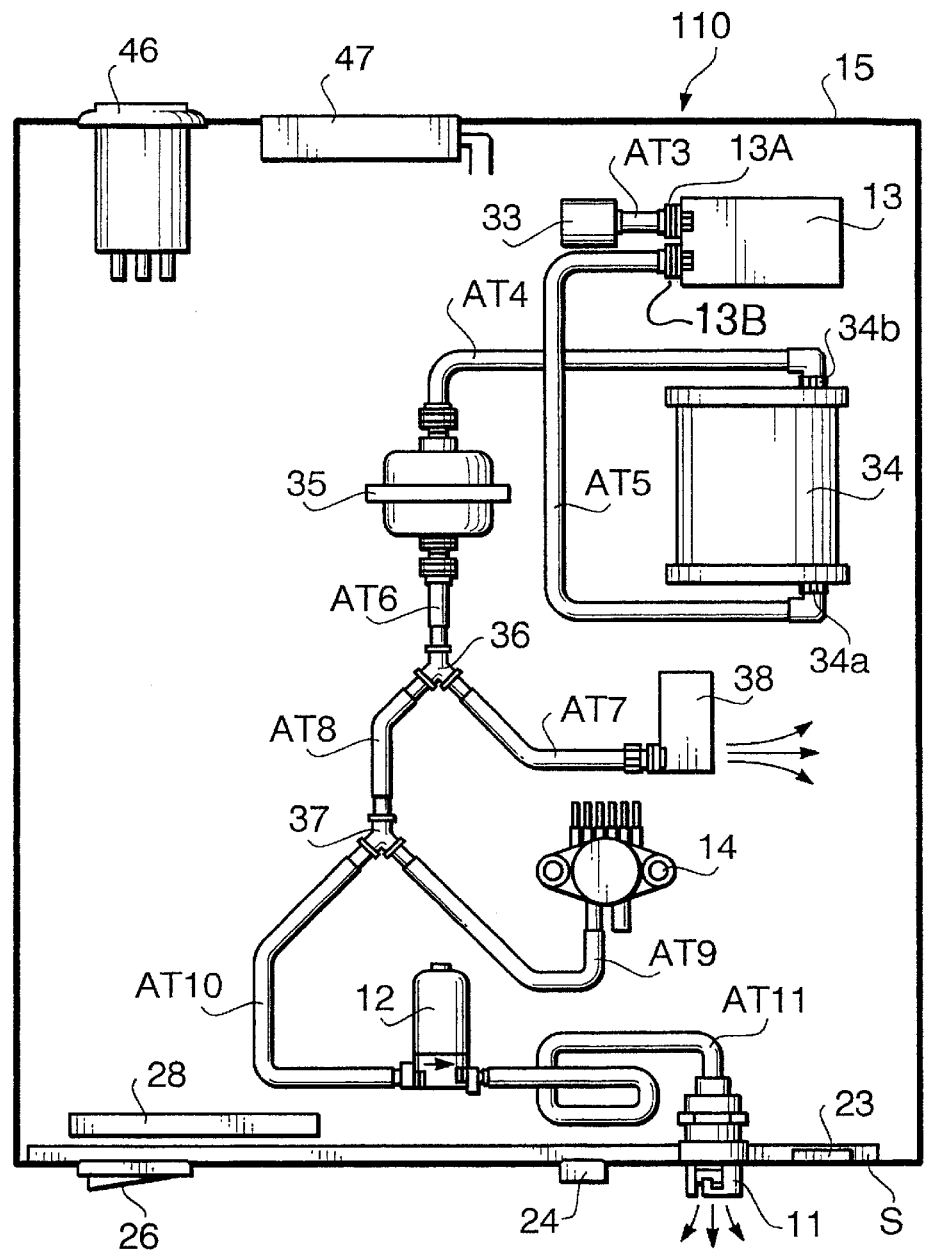

FIG. 3 schematically shows an arrangement of main elements inside the air feeding device 110, when an upper panel thereof is removed and viewed from the top. For the sake of simplicity, electrical circuits and wires are omitted in FIG. 3. As described above, on a wall of the casing 15, the AC inlet 46, the DC fan 47, the power switch 26, the operation panel S provided with the display 28, the connection port 11, and the connector 24 are provided.

Inside the casing 15, a sealed space for feeding the air is formed. Specifically, the sealed space is formed by: a compressor 13, an air tube AT5, an air tank 34, an air tube AT4, an air filter 35, an air tube AT6, a Y-joint 36, an air tube AT7, a pressure control valve 38, an air tube AT8, a Y-joint 37, an air tube AT9, a pressure sensor 14, an air tube AT10, and a discharging valve 12. The air enclosed in the sealed space is discharged from the connection port 11 via the air tube AT1.

The sealed space between the air filter 35 and the discharging valve 12 is branched, by the joint 36 and the air tube AT7, towards the pressure control valve 38, and by the joint 37 and the air tube AT9 towards the pressure sensor 14. It should be noted that the air tubes AT6, AT7 and AT8 communicate with each other through the joint 36. Further, the air tubes AT8, AT9 and AT10 communicate with each other through the joint 37.

The air enclosed in the sealed space is discharged when the pressure is adjusted, and the air is fed to the body cavity. The pressure control valve 38 is used for the former purpose, i.e., the pressure control valve 38 only opens when the pressure of the air in the sealed space is reduced. The discharging valve 12 is usually closed, and is opened only when the air feeding switch 22 or the foot switch 25 are operated.

In the first embodiment, a silencer 33 is provided for reducing noise when the compressor 13 operates. Specifically, the silencer 33 is coupled to the air intake 13A of the compressor 13 via the air tube AT3. When the compressor 13 starts operating, the air is introduced, via the silencer 33 and the air tube AT3, from the intake 13A of the compressor 13, and fed into the sealed space through an outlet 13B of the compressor 13, thereby the pressure in the sealed space is increased.

The air tank 34 is provided for enlarging the volume of the sealed space. The volume of the air tank 34 is much larger than the sum of the volumes of the air tubes AT4 through AT10. The air tank 34 is provided with connectors 34a and 34b on opposite surfaces, respectively, and the air tube AT5, which connects the outlet of the compressor 13, is connected to the connector 34a which is located farther from the compressor 13 than the connector 34b is.

The air filter 35 removes the dust existing in the sealed space.

The pressure inside the sealed space is measured by the pressure sensor 14.

When the enter switch 23 is turned ON, the compressor 13 and the pressure control valve 38 are driven to adjust the pressure in the sealed space in accordance with a set pressure. Specifically, if the pressure inside the sealed space (which will be referred to as an actual sealed space pressure Ps), which is detected by the pressure sensor 14, is lower than a pressure (which will be referred to as an objective pressure Po) for obtaining the set discharge pressure (which will also be referred to as the target discharge pressure Pt), the compressor 13 is driven and the pressure control valve 38 is closed. If the pressure inside the sealed space is higher than the objective pressure Po, the compressor 13 stops operating, and the pressure control valve 38 is opened. If the pressure Ps inside the sealed space coincides with the objective pressure Po, the compressor 13 does not operate, and the pressure control valve 38 is closed.

The discharging valve 12 operates in response to operation of the air feeding switch 22 or the foot switch 25. When the discharging valve 12 opens, the air is discharged from the connection port 11 via the air tube AT11.

Figure 4:
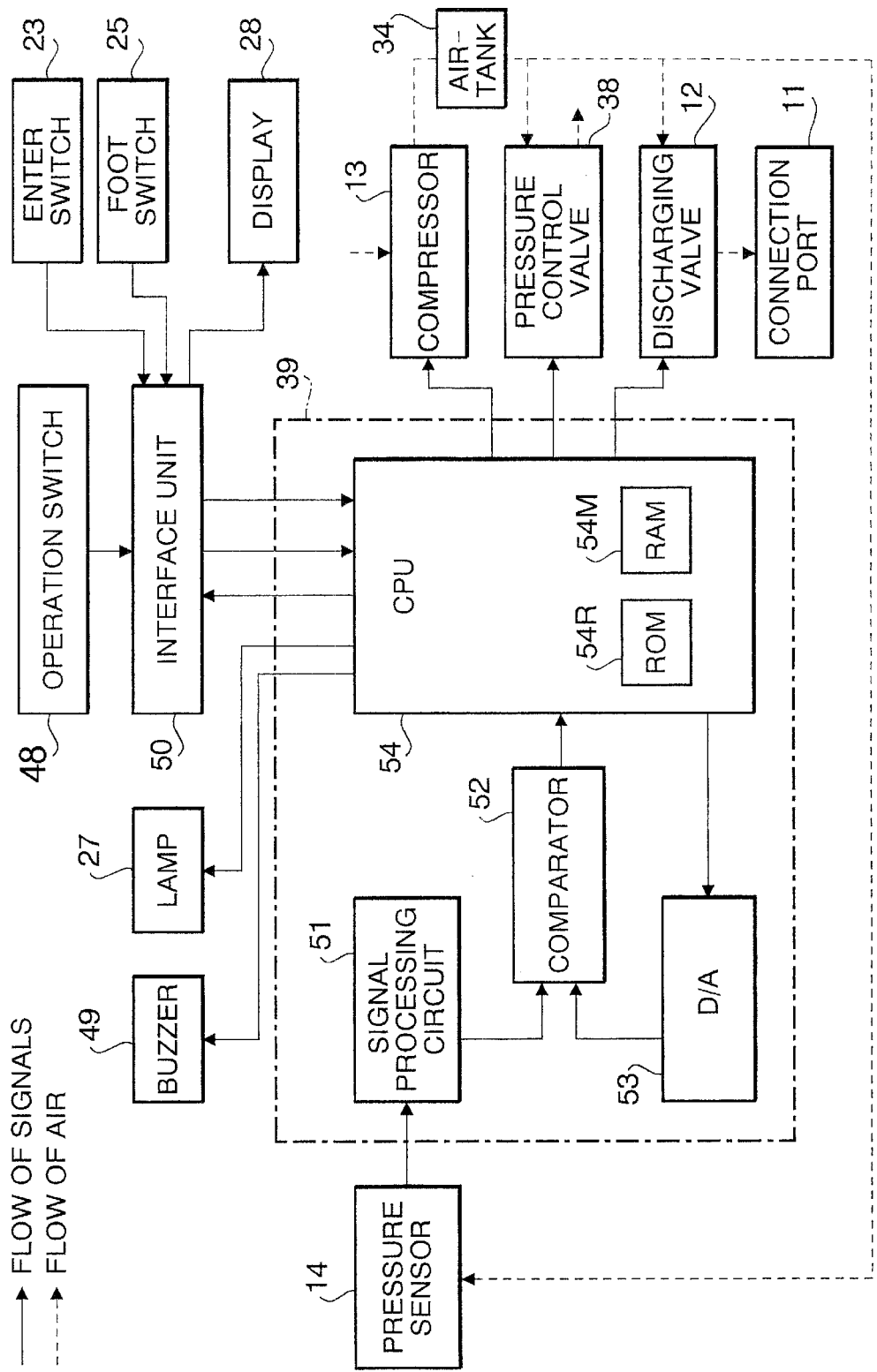
FIG. 4 is a block diagram illustrating a control system and air flow of the air feeding device according to the first embodiment.

FIG. 4 is a block diagram illustrating a control system and air flow of the air feeding device 110 according to the first embodiment. In FIG. 4, the flow of signal/data is indicated by solid lines, and the flow of the air is indicated by broken lines. The control system is provided with a controller 39, which includes a signal processing circuit 51, a comparator 52, a D/A converter 53, and a CPU (Central Processing Unit) 54. The controller 39 controls the operation of the entire system of the air feeding device 110. The CPU 54 outputs driving signals to the piezo-electric buzzer 49, a lamp 27, the compressor 13, the pressure control valve 38, and the discharging valve 12.

An operation switch unit 48 outputs predetermined signals in response to the operation of the air feeding switch 22, the short pulse switch 29, the long pulse switch 30, the UP switch 31 or the DOWN switch 32 (see FIG. 1). The signals generated by the operation switch unit 48 and the foot switch 25 are transmitted to the CPU 54 via an interface unit 50. The interface unit 50 applies predetermined signal processing/converting operations and outputs signals suitable to be processed by the CPU 54. The interface unit 50 determines the currently set discharge pressure in accordance with the signals generated in response to the operation of the UP and DOWN switches 31 and 32, and controls the dispaly 28 to display the same.

The signal output by the pressure sensor 14 is input into the signal processing circuit 51, and a predetermined signal processing operation (e.g., noise reduction) is applied. Then, the processed signal is input into one port of the comparator 52. The signal representing the target discharge pressure Pt set by the UP and DOWN switches 31 and 32 is converted into a signal representing the objective pressure in the sealed space, and is transmitted from the CPU 54 to the D/A converter 53 which outputs an analog voltage value. The analog voltage value output by the D/A converter 53 is input to the other input port of the comparator 52.

The comparator 52 compares the voltage output by the signal processing circuit 51 and the voltage output by the D/A converter 53. The comparator 52 outputs a difference between the voltage values which is converted into a signal having a value which can be processed by the CPU 54, then the converted signal representing the voltage difference is transmitted to the CPU 54. The CPU 54 temporarily stores the transmitted signal in a RAM 54M as comparison data.

When the enter switch 23 is ON,. the CPU 54 determines whether the pressure Ps in the sealed space is equal to the objective pressure Po in accordance with the comparison result stored in the RAM 54M. If the pressure Ps in the sealed space is different from the objective pressure Po, the CPU 54 drives the compressor 13 and/or the pressure control valve 38 to adjust the pressure Ps in the sealed space so as to coincide with the objective pressure Po.

It should be noted that, if the voltages compared by the comparator 52 are different but substantially equal, the operation of the compressor 13, and opening/closing of the pressure control valve 38 may repeat within a relatively short period of time (i.e., a so-called hunting phenomenon). In order to avoid such a situation, the comparator 52 is constituted to have a predetermined dead band.

The piezo-electric buzzer 49 is driven to buzz in accordance with the switch operations. The lamp 27 is lit when the air feeding device 110 is in the stand-by condition.

Through the AC inlet 46 and the main switch 26, the electric power is supplied to a power circuit (not shown), from which the electrical power is supplied to the display 28, the pressure sensor 14, the CPU 54, the compressor 13, the pressure control valve 38, and the discharging valve 12.

Figure 5:
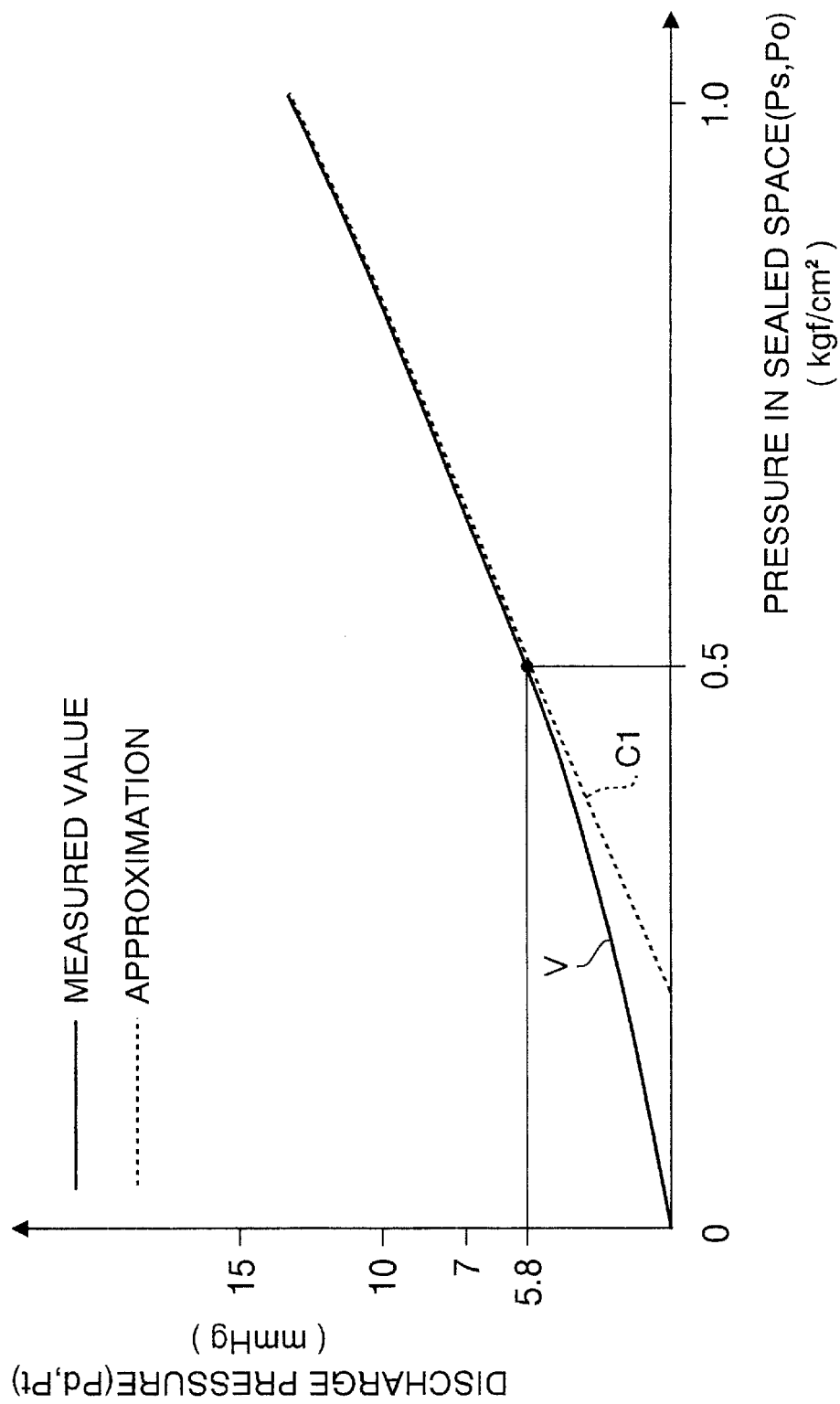
FIG. 5 shows a graph illustrating a relationship between the pressure in a sealed space and a discharge pressure according to the first embodiment.

FIG. 5 is a graph showing a relationship between the discharge pressure (which will be represented by Pd) and the pressure Ps in the sealed space. It is assumed that the discharge pressure Pd is a peak value of a pressure of the air at the outlet 19 of the forceps channel 18 of the endoscope 20. A unit of the discharge pressure in FIG. 5 is mmHg, and a unit of the objective pressure is kgf/cm². This relationship is stored in a ROM 54R in FIG. 4.

According to experiments, the relationship is represented by a curve V in FIG. 5. As shown in FIG. 5, the discharge pressure Pd and the pressure Ps have one-to-one correspondence. It should be noted that FIG. 5 is used as a graph representing a relationship between the target discharge pressure Pt and the objective pressure Po. That is, once a value of the target discharge pressure Pt is determined, the corresponding value of the objective pressure Po to be achieved is determined from FIG. 5.

Practically, the discharge pressure of 7 mmHg or less is hardly used. Thus, if the above range is ignored, the relationship represented by the curve V can be approximated by a straight line C1 (indicated by a broken line). The line C1 is expressed as follows:

$$Pd = aPs + b \tag{1}$$

where, Pd represents the discharge pressure Ps represents the pressure in the sealed space, and "a" and "b" are coefficients. In the example shown in FIG. 5, a=19.6 and b=−4.

From equation (1), the following equation (2) for determining the objective pressure Po from the target discharge pressure Pt is obtained.

$$Po = (Pt - b)/a \tag{2}$$

Thus, the objective pressure to be achieved can be calculated from the discharge pressure set by an operator in accordance with equation (2).

Figure 6:
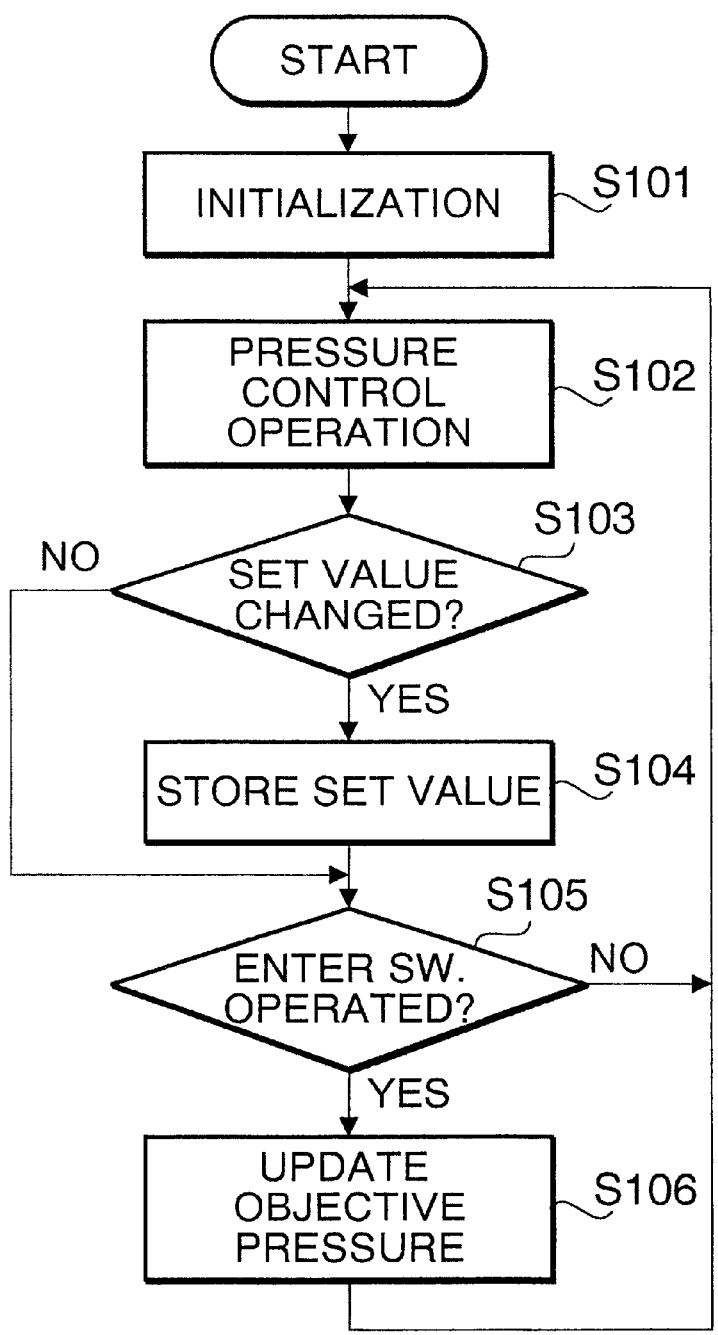
FIG. 6 is a flowchart illustrating the pressure control operation.

FIG. 6 is a flowchart illustrating the operation of the air feeding device 110. The procedure shown in FIG. 6 starts when the main switch 26 is turned ON.

In S101, an initialization process is performed. In the initialization process, the target discharge pressure Pt is set to a default value, and the discharge pressure (i.e., the default target value) Pt is displayed on the display 28. It should be noted that the default value of the discharge pressure is stored in the ROM 54R of the CPU 54. In S102, apressure control operation is performed. In the pressure control operation, the pressure in the sealed space is controlled so that the actual pressure Ps of the sealed space is equal to the objective pressure Po corresponding to the currently set discharge pressure Pt according to the equation (2). That is, the compressor 13 and/or the valve 38 are driven so that the pressure Ps in the sealed space coincides with the objective pressure Po. If the pressure Ps in the sealed space coincides with the objective pressure Po, operation of the compressor 13 is terminated, and the valve 38 is closed, and the lamp 27 is lit to indicate that the air feeding device is ready to discharge the air.

In S103, it is judged whether the UP switch 31 or the DOWN switch 32 is operated to change the setting of the discharge pressure Pt. If the setting of the discharge pressure Pt is changed, the value of the discharge pressure Pt is displayed on the display device 28.

When the setting of the discharge pressure is changed, the new setting of the discharge pressure Pt is temporarily stored in the RAM 54M (S104).

In S105, it is judged whether the enter switch 23 is operated. If the enter switch 23 has not yet been operated after the pressure value is changed, control skips S106, and accordingly, the objective pressure value Po is not changed. If the enter switch 23 is operated (S105: YES), then control goes to S106, where the CPU 54 determines a new objective pressure Po corresponding to the currently set target discharge pressure Pt in accordance with equation (2) stored in the ROM 54R, and input the new objective pressure Po to the D/A converter 53.

Then, control proceeds to S102, where the pressure Ps in the sealed space is adjusted in accordance with the changed objective pressure Po that corresponds to the currently set discharge pressure Pt. The above procedure is repeated until the main switch 26 is turned OFF.

According to the first embodiment, the pressure Ps in the sealed space can be set to an appropriate pressure (Po) corresponding to a desired discharge pressure Pt without discharging the air from the outlet of the forceps channel of the endoscope.

Second Embodiment

In the first embodiment, the relationship between the discharge pressure Pd (Pt) and the pressure Ps (Po) in the sealed space is approximated by a single linear function. The present invention is not limited to such an approximation, but the relationship may be expressed in various ways.

Figure 7:
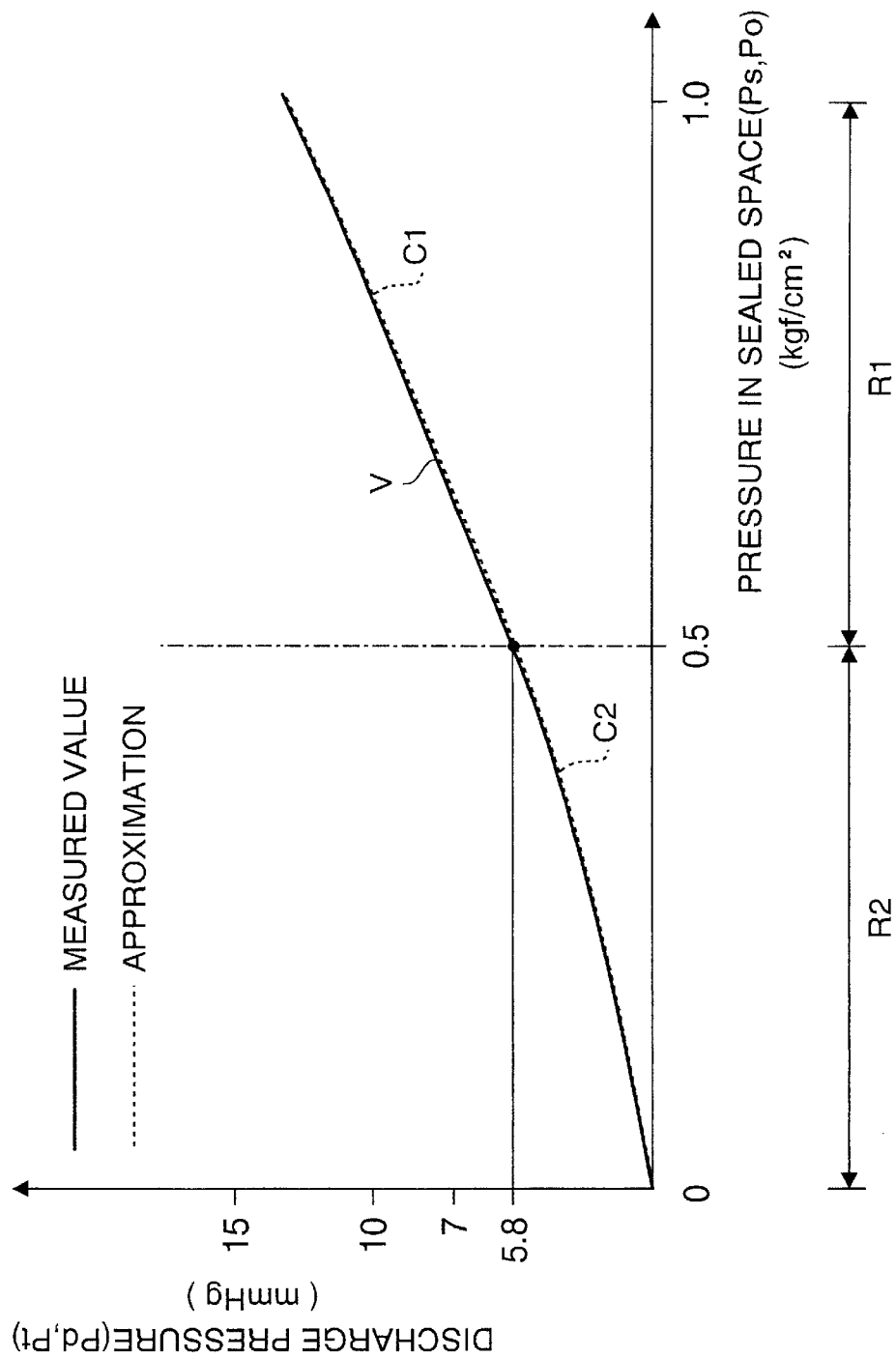
FIG. 7 shows a graph illustrating a relationship between the pressure in a sealed space and a discharge pressure according to a second embodiment.

FIG. 7 is a graph showing the experimental relationship between the pressure in the sealed space (V) which is similar to that in FIG. 5, and another approximation according to the second embodiment.

In this example, the curve V is divided into two segments at a position "T" where the pressure Ps (Po) of the sealed space is 0.5 Kgf/cm², and two approximate expressions are assigned to respective segments.

Specifically, the relationship in a right-hand side area R1 in FIG. 7 is approximated by the expression (1) similarly to the first embodiment (C1). Further, the relationship in a left-hand side area R2 in FIG. 7 is approximated by a quadratic curve C2 which is expressed by equation (3) below.

$$Pd = d \cdot Ps^2 \tag{3}$$

where, Pd represents a discharge pressure, Ps represents the pressure in the sealed space, and "d" is a coefficient. In the example shown in FIG. 7, d=23.2. The equation (3) can be understood to represent a relationship between the target discharge pressure Pt and the objective pressure Po in the sealed space to be achieved.

Thus, from equation (3), equation (4) below is obtained.

$$Po=(Pt/d)^{1/2} \qquad (4)$$

According to the second embodiment, even when a relatively low discharge pressure Pt is desired, the objective pressure Po to be achieved can be calculated, in accordance with equation (4), from the discharge pressure set by the operator.

It should be noted that the approximate expression is not necessarily be quadratic function, but can be N-th polynomial (5).

$$Pd=f(Ps)=aPs^n+bPs^{n-1}+cPs^{n-2}+\ldots+nPs+m \qquad (5)$$

where, "a", "b", . . . "n" are coefficients, and "m" is a constant.

In this case, equation (6) gives an objective pressure from a desired discharge pressure.

$$Po=f^{-1}(Pt) \qquad (6)$$

Third Embodiment

FIG. 8 is a perspective view of the air feeding system 300 according to the third embodiment of the invention. The constitution is substantially the same as the first embodiment shown in FIG. 1 except that, in the third embodiment, an endoscope system 320 is provided, and the air feeding device 310 is provided with a unit changing button Q for changing a unit of the pressure displayed on the display 28. The unit can be switched among [mmHg], [Pa] and [Kgf/cm²]. When the unit is changed, the values displayed on the display device 28 are changed accordingly.

FIGS. 9A–9C show exemplary display of pressures on the window 28A of the display 28. On a first line (upper line) of the display window 28A, a set value of the target discharge pressure Pt is displayed, and on a second line (lower line), a measured (actual) discharge pressure Pd is displayed in association with the unit. In the third embodiment, a unit [mmHg] is used as a default unit. By operating the UP switch 31 and/or DOWN switch 32, the upper numeral (i.e., the set value) of the target discharge pressure Pt can be changed. In FIG. 9A, 4.5 mmHg is the currently set target discharge pressure Pt, while 4.0 mmHg is the previously detected discharge pressure Pd. When the unit changing button Q is operated, the display may be changed to ones shown in FIGS. 9B where a unit [Pascal] is used, and 9C where a unit [Kgf/cm²] is used.

FIG. 10 schematically shows an arrangement of main elements inside the air feeding device 310 according to the third embodiment, when viewed from the top. The arrangement of the air feeding device 310 is substantially the same as the first embodiment shown in FIG. 3 except that a joint 58, air tubes AT12 and AT13, a dynamic sensor 57 are further provided. The joint 58 is connected at the downstream side end of the air tube AT11. One end of the air tubes AT12 and AT13 are also connected to the joint 58 so that the air fed through the air tube AT11 is branched to the air tubes AT12 and AT13. The other end of the air tube AT13 is connected to the connection port 11, and accordingly, the air fed through the air tube AT11 is directed to the endoscope via the joint 58, air tube AT13 and the connection port 11. The air tube AT12 directs the air fed through the air tube AT11 to the dynamic sensor 57 which detects the pressure of the air discharged from the air tube AT13. Based on thus detected pressure, the discharge pressure at the outlet of the forceps channel of the endoscope is detected.

FIG. 11 is a block diagram illustrating a control system and air flow of the air feeding device 310 according to the third embodiment. In FIG. 11, the flow of signal/data is indicated by solid lines, and the flow of the air is indicated by broken lines.

The control system of the air feeding device 310 is substantially the same as that of the first embodiment shown in FIG. 4 except that, in the air feeding system 310, the dynamic sensor 57 described above, a second signal processing circuit 55 are further provided.

When the enter switch 23 is ON, the CPU 54 determines whether the pressure Ps in the sealed space is equal to the objective pressure Po in accordance with the comparison data which represents a difference therebetween and is stored in the RAM 54M. If the pressure Ps in the sealed space is different from the objective pressure Po, the CPU 54 stores data representing the objective pressure Po corresponding to the currently set target discharge pressure Pd which has been stored in a RAM 54D. Then, the CPU 54 drives the compressor 13 and/or the pressure control valve 38 so that the pressure Ps in the sealed space coincides with the objective pressure Po.

When the discharging valve 12 is opened and the air is discharged, the discharge pressure at the outlet of the air tube AT12 is detected using the dynamic sensor 57. The dynamic sensor 57 outputs a signal corresponding to the pressure of the air discharged from the air tube AT12, which is transmitted to the second signal processing circuit 55. The second signal processing circuit 55 detects the peak value of the discharge pressure at the outlet of the air tube AT12 which corresponds to the discharge pressure Pd at the outlet of the forceps channel of the endoscope. Thus obtained peak value of the discharge pressure Pd is transmitted to the CPU 54. Then, the CPU 54 transmits a signal for displaying the detected peak value of the discharge pressure Pd to the display unit 28 via the interface unit 50.

FIG. 12 is a flowchart illustrating a procedure for displaying pressure values Pt and Pd on the display 28.

The procedure shown in FIG. 12 starts when the main switch 26 is turned ON. In S301, initial values of the target discharge pressure Pt and the detected discharge pressure Pd are displayed on the display unit 28 (see FIG. 13). It should be noted that the initial values are stored in the ROM 54R, and the stored values are used for display at the first stage. In this embodiment, the initial value of the target discharge pressure Pt is 4.0 mmHg, and the initial value of the detected discharge pressure Pd is 0.0 mmHg since the air has not yet been discharged at this stage.

In S302, it is judged whether the target discharge pressure Pt has been changed. If the target discharge pressure Pt has been changed (S302: YES), control proceeds to S305.

In S305, the changed target discharge pressure Pt is displayed on the first line in the display window 28A of the display unit 28. Simultaneously, a question mark "?" is also displayed when the discharge pressure has been changed. The question mark "?" remains displayed until the change is established by operating the enter key 23. Since the air is not discharged, the detected discharge pressure Pd displayed on the second line of the display window 28A remains unchanged.

FIGS. 14A–14C show examples of the display window 28A when the discharge pressure is changed. FIG. 14A shows a condition where the target discharge pressure Pt is set to 4.0 mmHg, and the air has not been discharged, detected pressure being 4.0 mmHg. If the UP button 31 is depressed once in the condition shown in FIG. 14A, the question mark "?" is displayed next to the character string "SETING" and the changed (increased) target discharge pressure 4.1 mmHg is displayed, while the detected pressure is unchanged. If the DOWN button 32 is depressed once in the condition shown in FIG. 14A, the question mark "?" is displayed next to the character string "SETING" and the changed (decreased) discharge pressure 3.9 mmHg is displayed, while the detected pressure is unchanged.

FIGS. 15A and 15B show examples of the display window 28A when the target discharge pressure Pt is changed quickly. When the UP button 31 or the DOWN button 32 is held depressed for more than a predetermined period (e.g., 1.5 sec.), the target discharge pressure Pt is started to change subsequently while the UP button 31 or the DOWN button 32 is held depressed. Accordingly, the target discharge pressure Pt is changed quickly. In this case, the question mark "?" is displayed similarly to the cases shown in FIGS. 14B and 14C, and further, an arrow "↑" or "↓" is displayed next to the pressure value. The arrow "↑" indicates the target discharge pressure Pt is being increased continuously and quickly, and the arrow "↓" indicates the target discharge pressure Pt is being decreased continuously and quickly. The arrows are extinguished from the display window 28A when the UP switch 31 or the DOWN switch 32 is released (turned OFF).

When the operator depresses the enter switch 23, the target discharge pressure Pt set during a loop of S301, S305 and S306 is established. That is, when the enter switch 23 is turned ON, control proceeds from S306 to S307.

In S307, the question mark "?" is extinguished from the display 28, and the pressure Ps in the sealed space is set to the objective pressure Po which is determined in accordance with the relationship shown in FIG. 5. Alternatively, the relationship shown in FIG. 7 can also be utilized. Thus, the relationship can be expressed by equation (2) or (4). Further alternatively, the relationship may be expressed by equation (6).

FIGS. 16A and 16B show the display window 28A illustrating the above. As shown in FIG. 16A, when the discharge pressure is changed but the enter key 23 has not yet been operated, the question mark "?" is displayed. When the enter key 23 has been operated, as shown in FIG. 16B, the question mark "?" disappear, and at this stage, the pressure Ps in the sealed space is adjusted.

In S302, if it is judged that the target discharge pressure has not been changed (S302: NO), it is judged whether the air feeding switch 22 is operated (S303). If the air feeding switch 22 is not operated (S303: NO), control returns to S302. If the air feeding switch 22 is operated (S303: YES), control proceeds to S304.

In S304, the air is discharged. The discharge pressure is detected by the dynamic sensor 57, and the detected discharge pressure Pd displayed in the display window 28A is updated. In this case, since the setting of the target discharge pressure Pt has not been changed, the discharge value set by the user remains unchanged in the display window 28A.

FIGS. 17A and 17B show the display window 28A before and after the air is discharged, respectively.

The above procedure is repeated until the main switch 26 is turned OFF.

According to the third embodiment, the operator can confirm the currently set target discharge pressure Pt, and a discharge pressure Pd previously discharged.

Further, since the mark "?" is displayed when the setting of the target discharge pressure Pt is changed but the enter key 23 has not yet been depressed, the user can be informed that the setting of the target discharge pressure Pt is being changed.

Since the arrow mark "↑" or "↓" is displayed when the UP button or DOWN button is held depressed for a certain period of time, the operator can confirm that the setting of the discharge pressure Pt is largely changed with respect to the previous setting.

Furthermore, since the setting of the target discharge pressure Pt and the previously measured discharge pressure Pd are displayed with vertical alignment, the operator can easily confirm the difference therebetween when he or she changes the setting of the target discharge pressure Pt.

Still further, since the Q switch for changing the unit is provided, the operator can confirm and set the pressures with reference to the suitable unit.

It should be noted that, in the third embodiment, when the setting of the target discharge pressure Pt is being changed (but not established), the question mark "?" is displayed. The invention is not limited to this configuration, but any other method of indication can be alternatively or optionally employed. For example, instead of displaying the question mark "?", the displayed numeral and/or character string may be blinked.

The present disclosure relates to the subject matters contained in Japanese Patent Applications No. HEI 10-321970, filed on Nov. 12, 1998, No. HEI 10-325553, filed on Nov. 16, 1998, which are expressly incorporated herein by reference in their entireties.

What is claimed is:

1. An air feeding device for endoscope system in which air is compressed in a sealed space and discharged from an outlet of a tube connected to the sealed space, comprising:

a pressure sensor that detects a pressure of the air in the sealed space;

a pressure adjusting system that adjusts the pressure of air in the sealed space;

a pressure setting device through which an operator is capable of setting a target discharge pressure representing a discharge pressure to be obtained;

a memory storing a relationship between a target discharge pressure and a pressure in the sealed space; and a pressure controller that controls said pressure adjusting system in accordance with the air pressure detected by said pressure sensor, said target discharge pressure set by said pressure setting device and the relationship stored in said memory;

wherein said relationship includes an approximate expression, said pressure controller determining the pressure in the sealed space in accordance with said approximate expression.

2. The air feeding device according to claim 1, wherein said approximate expression is a polynomial.

3. The air feeding device according to claim 1, wherein said approximate expression is a linear expression.

4. The air feeding device according to claim 1, wherein said approximate expression is a quadratic.

5. The air feeding device according to claim 1, wherein said pressure adjusting system comprises a compressor for feeding external air into said sealed space.

6. The air feeding device according to claim 5, wherein said pressure adjusting system further comprises a pressure control valve connected to said sealed space, said pressure control valve operating to discharge the air in said sealed space to reduce the pressure in said sealed space.

7. The air feeding device according to claim 1, further comprising a second pressure sensor for measuring a pressure discharged from said sealed space.

8. The air feeding device according to claim 7, further comprising a display system which displays the discharge pressure set through said pressure setting device and the pressure detected by said second pressure sensor.

9. The air feeding device according to claim 8, wherein the target discharge pressure set through said pressure setting device and the pressure detected by said second pressure sensor are displayed vertically aligned.

10. The air feeding device according to claim 8, wherein the target discharge pressure set through said pressure setting device is displayed such that a first display condition when the target discharge pressure is being set but not established and a second display condition when the target discharge pressure has been established a nd is not being set are different.

11. The air feeding device according to claim 10, wherein a predetermined mark is displayed together with the target discharge pressure set through said pressure setting device in said first display condition, while said predetermined mark is extinguished in said second display condition.

12. The air feeding device according to claim 8, wherein said pressure setting device includes a first switch for increasing the target discharge pressure and a second switch for decreasing the target discharge pressure, the target discharge pressure being changed by a predetermined amount on each operation of said first or second switch, the target discharge pressure being changed continuously when said first or second switch being held depressed for a predetermined period.

13. The air feeding device according to claim 12, wherein a mark indicating continuous change of the discharge pressure is displayed together with the target discharge pressure set through said first or second switch when being held depressed for said predetermined period.

14. The air feeding device according to claim 8, wherein a latest discharge pressure set by said pressure setting device is displayed as the target discharge pressure set by said pressure setting device until the target discharge pressure is changed by said pressure setting device.

15. The air feeding device according to claim 8, wherein a latest pressure measured by said second pressure sensor is displayed as the pressure measured by said second pressure sensor.

16. The air feeding device according to claim 8, wherein one of a plurality of units is selectable for displaying the target discharge pressure set through said pressure setting device and the pressure measured by said pressure sensor.

17. The air feeding device according to claim 16, wherein said plurality of units include at least one of [mmHg], [Pa] and [Kgf/cm$^2$].

18. The air feeding device according to claim 8, wherein said relationship includes an approximate expression, said pressure controller determines the pressure to be achieved in said sealed space in accordance with said approximate expression and the target discharge pressure set through said pressure setting device.

19. The air feeding device according to claim 18, wherein said approximate expression is a polynomial.

20. The air feeding device according to claim 18, wherein said approximate expression is a linear expression.

21. The air feeding device according to claim 18, wherein said approximate expression is a quadratic.

22. The air feeding device according to claim 1, further comprising an air discharge valve connected between said sealed space and said tube, said air discharge valve being operated to open to discharge the air.

* * * * *